(12) United States Patent
Chen et al.

(10) Patent No.: US 6,186,990 B1
(45) Date of Patent: *Feb. 13, 2001

(54) TO A HUMAN BODILY FLUID COLLECTION DEVICE AND METHOD OF COLLECTING AND ABSORBING THE SAME

(75) Inventors: Chen-Hsiung Chen; Hung Shou Li, both of Tainan (TW); Mike Deni Lin; Gary Lin, both of Irvine, CA (US)

(73) Assignee: Reachgood Industrial Company, Irvine, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/012,566

(22) Filed: Jan. 23, 1998

(30) Foreign Application Priority Data

Feb. 5, 1997 (TW) .................................................. 86202216
Jun. 20, 1997 (TW) .................................................. 86210176

(51) Int. Cl.⁷ ............................. A61M 1/00; A61F 5/44; A61G 9/00

(52) U.S. Cl. .................. 604/349; 604/317; 604/329; 604/319; 604/330; 604/331; 604/332; 604/349; 604/350; 604/351; 604/352; 604/353; 4/451; 4/452; 4/453

(58) Field of Search .................................. 604/317, 319, 604/329–331, 349–353; 4/451–453

(56) References Cited

U.S. PATENT DOCUMENTS

| 3,344,789 | * 10/1967 | Arnold et al. ...................... 128/287 |
| 3,797,734 | 3/1974 | Fleury . |
| 4,179,367 | * 12/1979 | Barthell et al. . |
| 4,187,850 | 2/1980 | Gust . |
| 4,187,851 | 2/1980 | Hauser . |
| 4,790,834 | * 12/1988 | Austin .................................. 604/349 |
| 4,820,291 | * 4/1989 | Terauchi et al. .................... 606/349 |
| 4,840,625 | 6/1989 | Bell . |
| 4,990,145 | 2/1991 | Fleury . |
| 4,996,727 | * 3/1991 | Wyatt ....................................... 4/451 |
| 5,002,986 | * 3/1991 | Fujiura et al. ......................... 524/47 |
| 5,007,116 | 4/1991 | Yamamoto . |
| 5,116,139 | 5/1992 | Young et al. . |

(List continued on next page.)

FOREIGN PATENT DOCUMENTS

| 2268882 | * 1/1994 | (GB) .................................... 604/332 |
| 85/03428 | * 8/1985 | (WO) .................................... 604/349 |

OTHER PUBLICATIONS

Little John, published in Sep. through Dec. 1997 issue of the *Sporty's Pilot Shop*, p. 73.
Little J. Adapter, published in Sep. through Dec. 1997 issue of the *Sporty's Pilot Shop*, p. 73.

*Primary Examiner*—John G. Weiss
*Assistant Examiner*—Paul Shanoski
(74) *Attorney, Agent, or Firm*—Bacon & Thomas, PLLC

(57) ABSTRACT

A collection device for human bodily fluids includes an expandable, liquid permeable and insoluble pouch containing a proper volume of hydrophilic material. This hydrophilic material allows quick absorption of such fluids and turns into gelled material. The gelled material is then trapped inside the pouch preventing possible spill and back flow. The hydrophilic material with a proper volume only allows expansion up to the predetermined size of the pouch without the pouch breaking up into fragments. This pouch may be made of different shapes and materials in order to fit in different types of human bodily fluid collection devices and reduce possible leakage and back flow. The hydrophilic material can be a polymer and may have antibacterial properties to reduce bacteria growth. A one-way valve, snap-fit seal, or screw-on cap may be added for further enhanced prevention of leakage and back flow. The versatility of this pouch helps speeding up manufacturing processes and reducing overall production costs.

18 Claims, 2 Drawing Sheets

U.S. PATENT DOCUMENTS

| | | | |
|---|---|---|---|
| 5,267,989 | * 12/1993 | Moyet-Ortiz | 604/349 |
| 5,300,246 | 4/1994 | Yamamoto et al. . | |
| 5,318,549 | 6/1994 | Yang . | |
| 5,354,132 | 10/1994 | Young et al. . | |
| 5,404,999 | * 4/1995 | Bednar | 206/204 |
| 5,531,724 | * 7/1996 | Young et al. | 604/327 |
| 5,549,707 | * 8/1996 | Weaver | 604/317 |
| 5,698,840 | 12/1997 | Jurisch et al. . | |
| 6,070,277 | * 6/2000 | Thomas | 4/484 |
| 6,116,780 | * 9/2000 | Young et al. | 383/44 |

\* cited by examiner

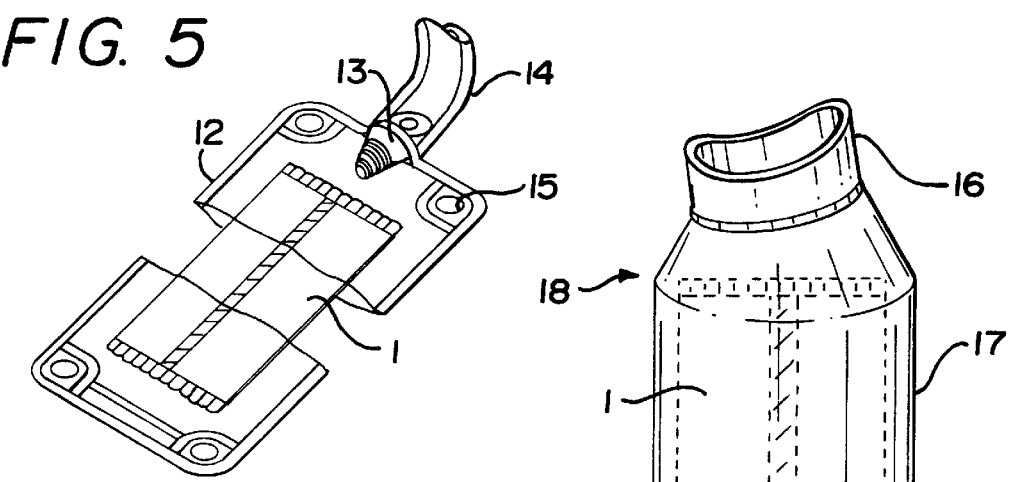
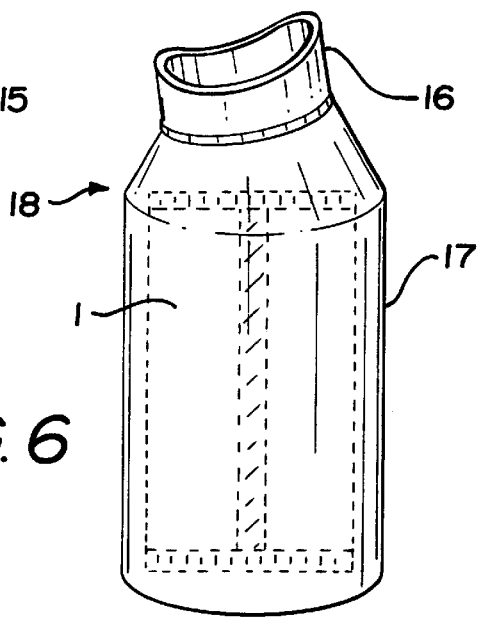
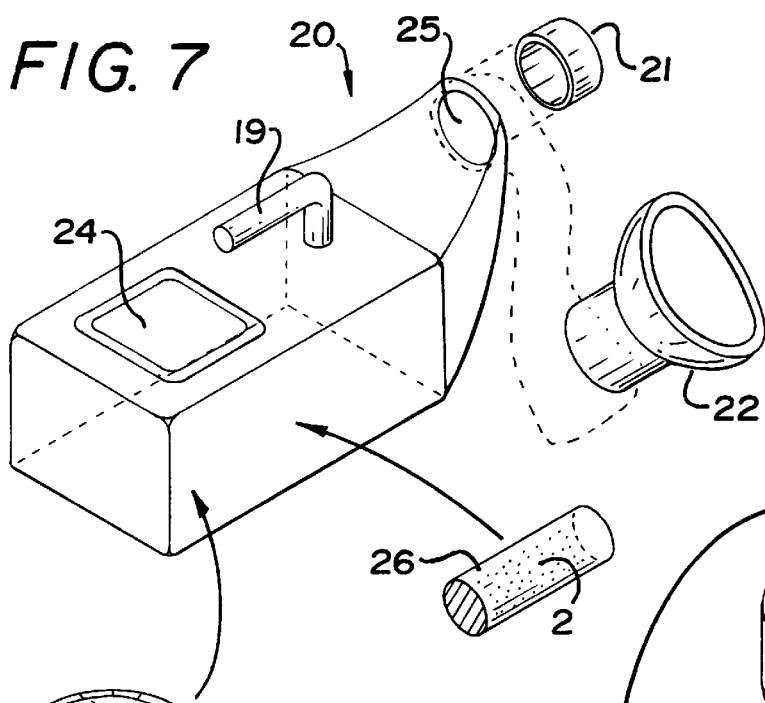
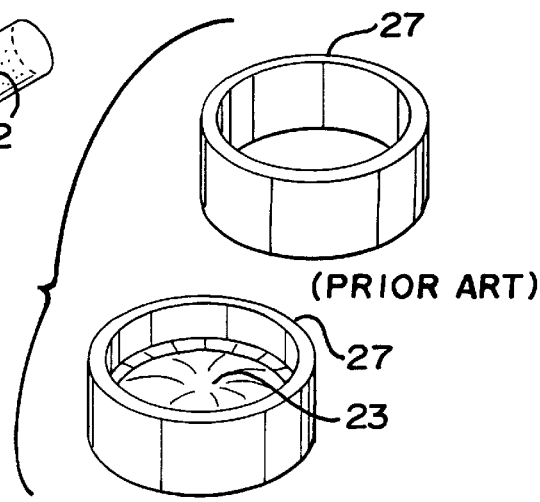

TO A HUMAN BODILY FLUID COLLECTION DEVICE AND METHOD OF COLLECTING AND ABSORBING THE SAME

BACKGROUND OF THE INVENTION

1. Field of the Invention

This invention relates to a method of producing a low-cost and versatile human bodily fluid collection device, particularly to one containing an expandable, liquid permeable and insoluble pouch which encloses a proper volume of hydrophilic powder or granular material for absorbing the fluid, and which is impermeable to and therefore serves to prevent the hydrophilic material from leaking out of the collection device. This volume of hydrophilic powder or granule serves the purpose of absorbing any incoming fluid to the device and turning them into an expanding pile of soft gel. This expandable, liquid permeable and insoluble pouch, which is allowed to freely expand to a pre-determined size, holds the expanding gel pile without breaking apart. Thus, this pouch prevents the gel to flow freely, to clog the inlet, to slip out of the collection device either from the inlet or puncture during usage.

2. Description of Related Art

A human bodily fluid collection device is generally used to collect urine, vomit, or other human bodily fluid from physically challenged persons and immobilized patients. Such a fluid collection device usually comes in different forms and shapes depending on the needs of particular persons or organizations that deem it to be suitable and comfortable, and, thus, attends to the proper relief and minimum strain and stress to the body. One form of human bodily fluid collection device is known as a urine collection reservoir, a urine drainage bag, or part of an catheter system, generally used in hospitals. U.S. Pat. No. 4,840,625 to Ramona R. Bell shows an external catheter system which consists of a urine collection reservoir, a urine collection inlet, a urine collection tube, and an external catheter for male use. The urine collection reservoir is mainly used to store urine up to its capacity and later drained to the sewage system. However, this type of reservoir has had its problems, such as the the problem that the urine may travel along the tube back to the source and thus cause possible infection, known as the urinary track infection (UTI). Another problem is that the reservoir, generally made of soft plastic material, faces the possibility of puncturing either during transport or by accidentally pinching the reservoir via sharp edges. Thus, the urine may leak and contaminate the surroundings. Also, the urine, if already infected from its source, may expose the persons within the perimeters to contamination. Yet another problem is that during draining of the liquid waste, there is a possibility of accidentally disconnecting the collection tube from the collection inlet, which will cause the urine to pour out from the inlet uncontrollably due to the pressure built-up of the existing urine inside the bag.

Also, a $2^{nd}$ type of urine collection unit as shown on U.S. Pat. No. 5,531,724 to Ruth E. Young has much better improvement to include a one-way valve which prevents back flow, and, gelling which turns the urine into gelled material and not allowing to flow backward. However, the drawback of such a device is that such a one-way valve is more costly to assemble during production since combining this one-way valve with the inlet nozzle and the collection bag itself requires precise molding or else leakage will occur. Besides, the gelled material can still leak out of the bag if the bag is punctured or torn open. Another problem lies within the design that this one-way valve is constructed, as stated in this patent, to close by itself upon contact with fluid and gelled material and preventing escape of both. This design does not prevent the escape of the hydrophilic material such as polymer particles from the collection unit before it turns into gelled material while this collection unit is been turned upside down during handling or transport.

Another form of human bodily fluid collection device is a light-weight, small, and portable urine collection bag or urinal, commonly used during traveling, camping and inside recreational vehicle and car. This type of urine collection device is shown in U.S. Pat. No. 5,318,549 to Chung-Rong Yang and U.S. Pat. No. 5,007,116 to Masao Yamamoto. Per U.S. Pat. No. 5,318,549 shows a fixed-rectangular-shaped absorbent material, which is enclosed inside a urine bag made of liquid impermeable paper material. The absorption of this type of material, similar to that of a sponge, is only limited to the porous space allowed within the material and small in its capacity to hold large amount of fluid. Since this type of material is not freely to expand, it hinders its capability to further absorb more liquid.

Per U.S. Pat. No. 5,007,116 shows yet another type of human bodily fluid collection device, called portable urinal. This urinal as devised consists of a urine-storage bag constructed of a water proof material and snap-fit seal that closes the upper portion of the urinal preventing spill, a pouch inside the bag constructed of water-permeable material containing water absorbent material. This water absorbent material upon contact with water will expand, turn into gel and break the pouch into fragments. This design poses few problems. One is that once the pouch breaks apart, the gel can move freely around inside the bag. Although the bag can be sealed from the upper portion, any puncture at any given location can still allow the gel to leak out of the bag. Second problem is associated with the comfort level of any person required to seal this bag manually and risk the possibility of contacting the bodily fluid waste. Then, if the bag is not full and is reused again, the seal needs to be reopened which also raises concern of possible human contact with the waste. Yet another problem is that before the urinal is sealed, there is possibility of spilling the gel during usage if the urinal is accidentally dropped or squeezed too hard from the outside. And, lastly, the snap-fit seal is much more difficult to manufacture and may lead to leaks and tears if not properly done so. Since the seal needs to be molded onto the soft plastic bag, it significantly weakens the structure of the bag itself during manufacturing. More stringent manufacturing procedures and quality controls are demanded and thus lead to higher manufacturing cost.

Another form of the bodily fluid collection device, known as the "Little John" as shown in FIG. 7, which is a widely used urinal in hospitals for many years. This urinal 20, intended to be portable, reusable, convenient and spill-proof, is constructed of durable hard plastic with a handle 19 for carrying, a screw-on cap 21 for covering and an optional "Lady J Adapter" 22 for female use. Although the cap can be screwed on to prevent spill, the disadvantage of this design is that during usage dropping this urinal will spill the urine before this cap can even be used. Also, when this Lady J Adapter is used, the cap can not be screwed on, which is another possibility of allowing urine to spill during usage or transport.

None of the above devices provides a complete assurance of preventing back flow, leakage and spill problems nor can it be cheaply manufactured and assembled if sufficient design is added to prevent these problems. It is, therefore, an object of the invention to devise a simple and yet useful method of collecting and absorbing the human bodily fluid that provides effective seal from leakage and back flow.

Yet another object of the invention is to provide largest capacity of absorption power while maintaining the device, if unused, small, compact, light-weight, and, most important of all, versatile and suitable for many types of human bodily fluid collection devices. A further object of the invention is to manufacture this method inexpensively and to increase its ease of transport, handling and storage.

SUMMARY OF THE INVENTION

This invention has been devised to offer a simple and yet useful method of collecting and absorbing human bodily fluid that prevent leakage and back flow by utilizing an expandable, liquid permeable and insoluble, pouch. Such pouch contains a proper volume of hydrophilic polymer powder or granule for absorbing the incoming fluid.

The size in diameter of these individual hydrophilic polymer powder is large enough and does not allowed to penetrate through the pouch. Hence, the problem of the powder leaking out before its use is very unlikely.

Yet when the powder is in contact with liquid, it absorbs such liquid and turns into expanded soft gel. The soft gel are contained inside the pouch with the size of such pouch predetermined to hold up all the expanded gel without break. Therefore, the problems of the fluid leaking, the gel clogging the collection inlet, the gel leaking out a punctured bag, or the gel flowing backward and spill out from the device inlet are controlled and eliminated.

Since the pouch is manufactured at a predetermined size which can expand and hold up to the size of the collection device, the capacity of its absorption is not reduced unlike that of a sponge. Yet another advantage of the pouch is the thin thickness of the material used, generally a top and a bottom layers combined, such as 2 layers of a non-woven cloth forming the bag. With the granular powder already small in diameter before contacting any liquid, spreading the powder inside the pouch makes the thickness unnoticeable. Therefore, the pouch with these absorbent powder is light in weight and space-saving.

Also, when these pouches are made into several shapes, such as rectangular, circular, elliptical, or cylindrical, they are suitable and versatile and can be used with any type of human bodily collection devices available now in the markets while minimizing any spill, leakage, and thus any discomfort of use.

Also, the cost of manufacturing any type of the above fluid collection devices are reduced significantly since these pouches can be mass manufactured and thereby reducing the cost of each pouch. Later, these pouches can be used with any urine collection device as specified and required by the users.

As in U.S. Pat. No. 5,531,724, the stated one-way valve can be made optional with the use or replacement of the present pouch invention, and, thus the manufacturing cost can be reduced.

Also, in U.S. Pat. No. 5,007,116, the snap-fit seal is not required at all since the pouch will hold back the material either in powder or gelled form, and, thereby, reducing extra manufacturing process and molding cost of the snap-fit seal.

Lastly, with the thin, light-weight, and spill-proof design of this pouch, the difficulties during transporting, handling and storage of such device are greatly eased.

BRIEF DESCRIPTION OF THE DRAWINGS

This present invention will be better understood by referring to the accompanying drawings, where in:

FIG. 5 illustrates the actual method of using this and insoluble pouch (FIG. 1) in a hospital urine collection bag;

FIG. 6 illustrates the actual method of using this and insoluble pouch (FIG. 1) inside a portable, disposable urinal consisting of both soft and hard plastic parts;

FIG. 7 illustrates the actual method of using this and insoluble pouch (FIG. 3) in a portable, reusable urinal consisting of hard plastic parts;

FIG. 8 illustrates the actual method of using this and insoluble pouch (FIG. 3) in a bedpan.

DETAILED DESCRIPTION OF THE PREFERRED EMBODIMENTS

Figure 1:
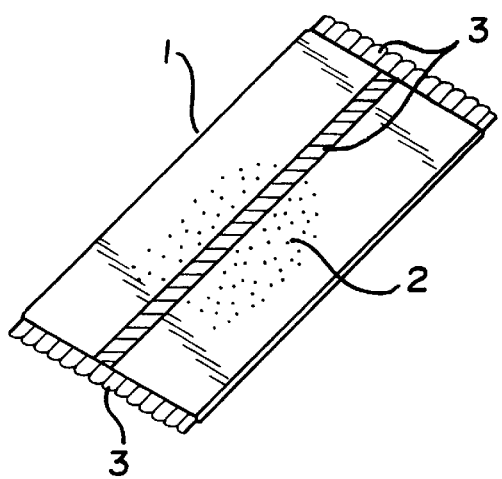
FIG. 1 illustrates an unused rectangular-shaped expandable, liquid permeable and insoluble pouch.

FIG. 1 illustrates a human bodily fluid absorbing pouch 1 in accordance with the principles of the invention. The pouch 1 constructed of a sheet of expandable, liquid permeable and insoluble material, such as a non-woven fabric. The granular hydrophilic absorbing powder 2, impermeable to the sheet, is placed flatly onto the sheet. Then the sheet is folded into a rectangle enclosing the powder 2 and sealed along seams 3, shown in FIG. 1, preventing the powder 2 from leaking out. It will be appreciated by those skilled in the at that the folded sheet can be sealed in many different ways so as to confine the power 2 from scattering and leaking out the pouch 1.

Figure 2:
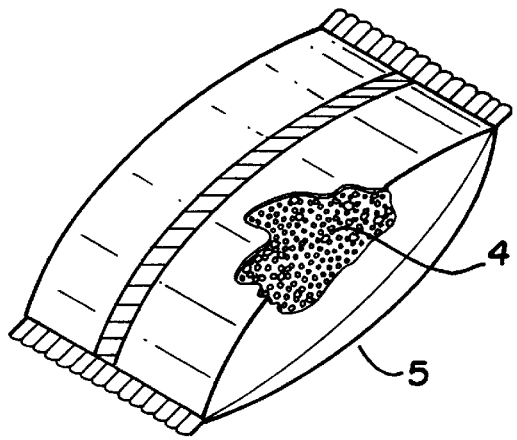
FIG. 2 illustrates the expanded rectangular-shaped liquid permeable and insoluble pouch after turning liquid into soft gel.

FIG. 2 illustrates the final shape 5 of the pouch 1 after the fluid is absorbed and turned into enlarged gelled particles 4 of larger diameter than the original powder 2. The gelled particles 4 are again restricted from passing through the sheet material. It is understood by those skilled in the art that although scattered gelled particles of semi-solid form are much easier to contain than liquid form, the present invention of the pouch 1 containing these gelled particles 4 is much simpler in design and can be picked up and disposed of with less effort than the gelled particles themselves.

Figure 3:
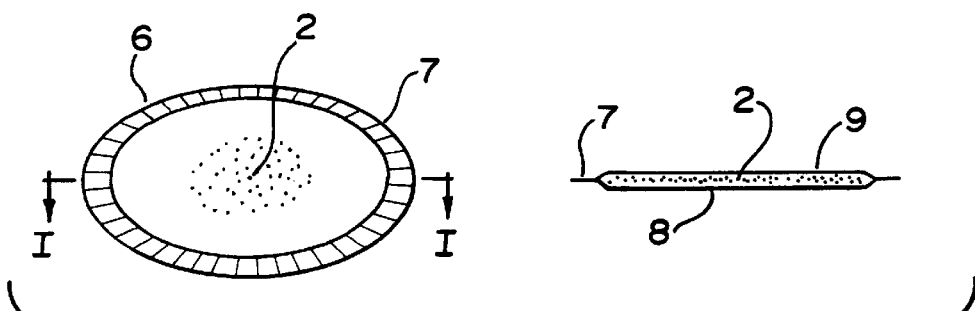
FIG. 3 illustrates an unused elliptically-shaped expandable, liquid permeable and insoluble pouch, and, its cross sectional view.

FIG. 3 illustrates yet another shape of the pouch 6 and its cross sectional view 9, taken along the line I—I, containing the powder 2. The pouch 6 is elliptically shaped and constructed of 2 sheets 8 of liquid permeable and insoluble material sealed along seam 7. Like FIG. 1, the powder 2 is not allowed to leak out.

Figure 4:
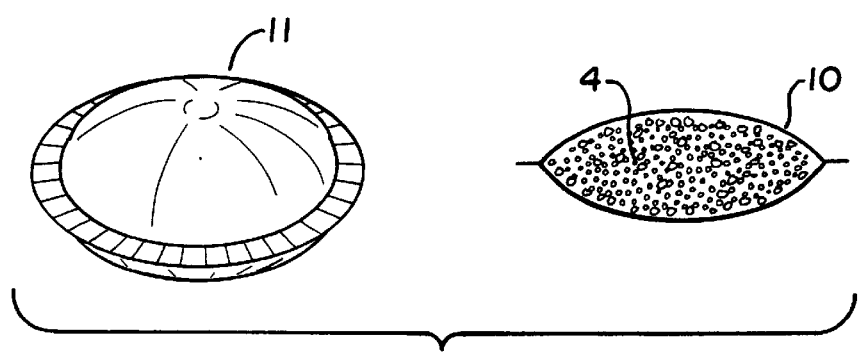
FIG. 4 illustrates an expanded elliptically-shaped liquid permeable and insoluble pouch after turning liquid into soft gel, and, its cross sectional view.

FIG. 4 illustrates the expanded shape 11 of the pouch 6 with its cross sectional view 10 showing the expanded gelled particles 4 trapped inside the pouch 6.

FIG. 5 illustrates a urine collection bag 12 utilizing the idea of the present invention. The collection bag 12 is constructed of a urine collection tube 14, a urine collection inlet 13, a collection pouch 1, and holes 15 for hanging the bag. The usefulness of the present invention can be clearly seen when the urine flows into the collection bag 12, the pouch 1 will absorb the urine and turn into expanded gelled pouch 5 as shown in FIG. 2. The pouch 5 will prevent the urine and urine gel from flowing backward into the tube 14 nor clogging the inlet 13. Also, even if the bag 12 is punctured, the pouch 1 will still hold back the powder 2 or gelled material 4, acting as a double protection. If required, the collection inlet 13 can be constructed with an optional one-way valve, as shown in U.S. Pat. No. 5,531,724, to prevent leakage of excess liquid inside the bag 12.

FIG. 6 yet illustrates another application of the present invention for use with a portable disposable urinal 18. The urinal 18 is constructed of a large adapter inlet 16, a liquid collection bag 17, and, the liquid absorbing pouch 1. The large adapter inlet 16 is made of hard plastic forming a contour shape which can be used by male or female, as indicated in U.S. Pat. No. 5,007,116. The liquid collection bag 17 is made of soft plastic material that is expandable to contain a predetermined volume of incoming urine. With the pouch 1 inside the bag 17, the incoming urine will turn into gelled form confined by the pouch 1 and not be allowed to spill out even if this urinal 18 is dropped or flipped upside down. It is appreciated that a snap-fit seal can be added to further enhance the comfort of not letting any residual urine from flowing out of the large adapter inlet 16. Despite the fact that this device 18 is used as a urinal, it can be appreciated by those skilled in the art that such device can be used as a vomit bag.

FIG. 7 illustrates yet another application of the present invention, a reusable urinal 20 utilizing the addition of the pouch 6. The urinal 20 is constructed of hard plastic material and, even with urine filled to the top, its shape will not deform. The urinal 20 has a handle 19, a screw-on cap 21 for sealing the inlet 25, an optional female adapter 22 fitting over the inlet 25, and a pouch 1 for absorbing urine or vomit. It is understood that without the pouch 6, the liquid inside the urinal 20 may still spill if it is dropped and the screw-on cap is not used. The same can happen if the female adapter 22 is inserted for use. With the pouch 6 put inside the urinal 20, while the urinal 20 is used, it constantly absorbs the incoming liquid and turns them into gelled pouch 23 not allowing spill. Spills can thus be minimized while the urinal 20 is carried to a dump site. The gelled pouch 23 can easily be disposed into a trash can without the liquid leaking out.

Another object of this invention is to include a large second opening 24, which is constructed into the urinal 20. The opening 24 can be open for disposing the used pouch 23.

Some reusable urinal may have a much smaller inlet 25. In this case, a pouch 26 of a skinnier shape, containing the hydrophilic powder 2, can be used so that when it is completely absorbed and expanded, the pouch 26 can be thrown out from inlet 25 and reused again.

Lastly, FIG. 8 illustrates the use of the pouch 6 with a bedpan 27 of a prior art. It is understood that the waste of a human consists not only solid waste form but usually associated with liquid waste which are channeled to the bedpan 27.

As indicated in U.S. Pat. No. 5,689,840 which is designed to be used at different orientation, can be made to be a greater comfort for the patients with the present invention. Although it does prevent some sort of leakage, it is not desirable that any liquid waste flowing around and inside the bedpan still spill onto the person using it while maneuvering over this bedpan.

With the pouch 6 enclosed inside the bedpan 27, any incoming liquid will immediately turned into gel and confined by the pouch 6. Thus, both the solid waste and the gelled pouch 23 can be easily disposed.

It is accordingly intended that the invention not be limited by the above description or accompanying drawings, but that it be defined solely as indicated in the appended claims.

What is claimed is:

1. A pouch for use with a human bodily fluid collecting device for the purpose of collecting and absorbing a bodily fluid, said pouch comprising:
   an expandable, liquid permeable and insoluble material forming said pouch and enclosing a hydrophilic material, said pouch being impermeable to the said hydrophilic material, wherein when a bodily fluid enters said pouch through said liquid permeable material, said hydrophilic material expands and turns into a soft gel, causing said pouch to expand without breaking apart and thereby contain said soft gel.

2. The pouch as claimed in 1 in which said expandable, liquid permeable and insoluble pouch comprises at least one type of material selected from the group consisting of a non-woven fabric, woven fabric, a sheet of paper, a perforated plastic film, and a porous plastic film.

3. The pouch as claimed in 1 in which said hydrophilic material is a polymer.

4. The pouch as claimed in 3 in which the said polymer absorbs liquid at a weight ratio of liquid to polymer of at least 20 to 1.

5. The pouch as claimed in 3 in which the polymer has a rate of completely absorbing 600 cubic centimeter of liquid in 15 seconds or less, or, equivalent volume of liquid in equivalent amount of time or less.

6. The pouch as claimed in 1 in which said hydrophilic material has antibacterial properties.

7. The pouch as claimed in 1 in which the said pouch is constructed to fit said collection device having one of the following shapes: rectangular, circular, elliptical, or cylindrical.

8. The pouch as claimed in 1 in which said pouch is used with at least one device selected from the group consisting of a urine collection reservoir, a portable urinal made of hard plastic, a portable urinal made of soft plastic, a portable urinal made of impermeable paper, and a bedpan.

9. A human bodily fluid collecting device for the purpose of collecting and absorbing said bodily fluid, comprising:
   a pouch comprising an expandable, liquid permeable and insoluble material forming said pouch and enclosing a hydrophilic material, said pouch being impermeable to the said hydrophilic material, wherein when a bodily fluid enters said pouch through said liquid permeable material, said hydrophilic material expands and turns into a soft gel, causing said pouch to expand without breaking apart and thereby contain said soft gel; and
   a container which has at least one opening inlet through which human bodily fluid enters said container, and which at least partially encloses said pouch to prevent direct contact with human body.

10. The human bodily fluid collecting device as claimed in claim 11 in which said container mean is selected from the group consisting of a urine collection reservoir, a portable urinal, a bedpan, a urostomy bag, an ileostomy bag, or an ostomy bag.

11. The human bodily fluid collection device as claimed in claim 10 in which said portable urinal is made of a portable urinal material selected from the group consisting of hard plastic, soft plastic, impermeable paper, and combinations of portable urinal materials.

12. The human bodily fluid collection device as claimed in claim 10 in which of said at least one opening is larger than a size of said pouch after said pouch has completely expanded to a predetermined size so that said pouch can be removed and replaced with a new unused pouch through said opening.

13. The human bodily fluid collection device as claimed in claim 10 in which said portable urinal has at least one second opening, wherein a size of said second opening is larger than a size of said pouch after said pouch has completely expanded to its predetermined size so that said pouch can be removed and replaced with a new unused pouch through said second opening.

14. The human bodily fluid collection device as claimed in claim 10 in which said collection reservoir is an intermittent catheter bag, a leg bag, or a night drainage bag.

15. The human bodily fluid collection device as claimed in claim 11 in which said at least one opening inlets of said container includes a member selected from the group consisting of a one-way valve, a snap-fit seal, and a screw-on cap.

16. A method of using a pouch for collecting and absorbing a human bodily fluid in a container, comprising the steps of:

providing a container including said pouch:

said pouch comprising an expandable, liquid permeable and insoluble material forming said pouch and enclosing a hydrophilic material, said pouch being impermeable to the said hydrophilic material, wherein when a bodily fluid enters said pouch through said liquid permeable material, said hydrophilic material expands and turns into a soft gel, causing said pouch to expand without breaking apart and thereby contain said soft gel;

introducing a human bodily fluid into said container through said at least one opening inlet;

allowing said fluid passing through said pouch and contact said hydrophilic material in response to contact between said pouch and said fluid;

causing said fluid to turn into said soft gel upon contact between said fluid and said hydrophilic material; and encapsulating said soft gel in said pouch to prevent said soft gel from escaping said pouch and said at least one opening inlet.

17. The method as claimed in claim 16, wherein said at least one opening inlet includes at least one one-way valve, and further comprising the step of enclosing said hydrophilic material within said pouch and placing said pouch within said container before the step of introducing said fluid into said container, thereby preventing said hydrophilic material from leaking out of said at least one opening inlet, and wherein the step of encapsulating said soft gel is carried out after the step of introducing said fluid into said pouch, thereby preventing a portion of said soft gel from clogging said at least one one-way valve.

18. The method as claimed in claim 17, wherein said hydrophilic material is a polymer and said step of causing said fluid to form said soft gel comprises the step of contacting said fluid with said polymer.

* * * * *